United States Patent
Zankowski et al.

(10) Patent No.: US 11,951,330 B2
(45) Date of Patent: *Apr. 9, 2024

(54) MULTILEAF COLLIMATOR CONE ENABLING STEREOTACTIC RADIOSURGERY

(71) Applicant: Varian Medical Systems, Inc., Palo Alto, CA (US)

(72) Inventors: Corey Zankowski, San Jose, CA (US); Sasa Mutic, St. Louis, MO (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/725,707

(22) Filed: Apr. 21, 2022

(65) Prior Publication Data
US 2022/0241616 A1 Aug. 4, 2022

Related U.S. Application Data

(60) Continuation of application No. 17/153,161, filed on Jan. 20, 2021, now abandoned, which is a division of application No. 16/399,828, filed on Apr. 30, 2019, now Pat. No. 10,974,071.

(51) Int. Cl.
*A61N 5/10* (2006.01)
*G21K 1/04* (2006.01)

(52) U.S. Cl.
CPC ........... *A61N 5/1045* (2013.01); *G21K 1/046* (2013.01); *A61N 5/1031* (2013.01); *A61N 5/1049* (2013.01)

(58) Field of Classification Search
CPC ............................. A61N 5/1045; G21K 1/046
See application file for complete search history.

(56) References Cited

U.S. PATENT DOCUMENTS

| | | | |
|---|---|---|---|
| 8,637,841 B2 | 1/2014 | Prince et al. | |
| 8,890,100 B2 | 11/2014 | Huntzinger et al. | |
| 10,974,071 B2 * | 4/2021 | Zankowski | G21K 1/046 |
| 2009/0074148 A1 | 3/2009 | Echner | |
| 2012/0043482 A1 | 2/2012 | Prince et al. | |
| 2014/0112451 A1 | 4/2014 | Figueroa Saavedra et al. | |

(Continued)

FOREIGN PATENT DOCUMENTS

EP        1720173 A1     11/2006

OTHER PUBLICATIONS

Fiveash et al; A Phase II Trial of Virtual Cone Trigeminal Neuralgia Radiosurgery; University of Alabama at Birmingham; ClinicalTrials.gov, NIH, U.S. National Library of Medicine; https://classic.clinicaltrials.gov/ct2/show/NCT02708810;; Aug. 2, 2016.

(Continued)

*Primary Examiner* — Chih-Cheng Kao
(74) *Attorney, Agent, or Firm* — Harness, Dickey & Pierce, P.L.C.

(57) ABSTRACT

An apparatus includes a first multileaf collimator comprising a plurality of pairs of beam-blocking leaves each comprising an end portion. The end portions of beam-blocking leaves of two adjacent pairs are configured to collectively form an aperture when the two adjacent pairs of beam-blocking leaves are closed. The aperture may be sized and shaped to allow a radiation beam to pass through for radiosurgery.

18 Claims, 8 Drawing Sheets

(56) References Cited

U.S. PATENT DOCUMENTS

| | | | |
|---|---|---|---|
| 2015/0273239 A1* | 10/2015 | Hsu | A61N 5/1045 378/150 |
| 2017/0197094 A1 | 7/2017 | Popple | |
| 2018/0104511 A1 | 4/2018 | Hsu et al. | |
| 2019/0091489 A1 | 3/2019 | Xiao et al. | |
| 2021/0093892 A1 | 4/2021 | Wang et al. | |

OTHER PUBLICATIONS

Popple et al., The virtual cone: A novel technique to generate spherical dose distributions using a multi-leaf collimator and standardized control-point sequence for small target radiosurgery, Advances in Radiation Oncology, Feb. 21, 2018, 27 pages.

PCT, International Search Report and Written Opinion of the International Searching Authority in PCT/US2020/030326 dated Aug. 3, 2020, 12 pages.

* cited by examiner

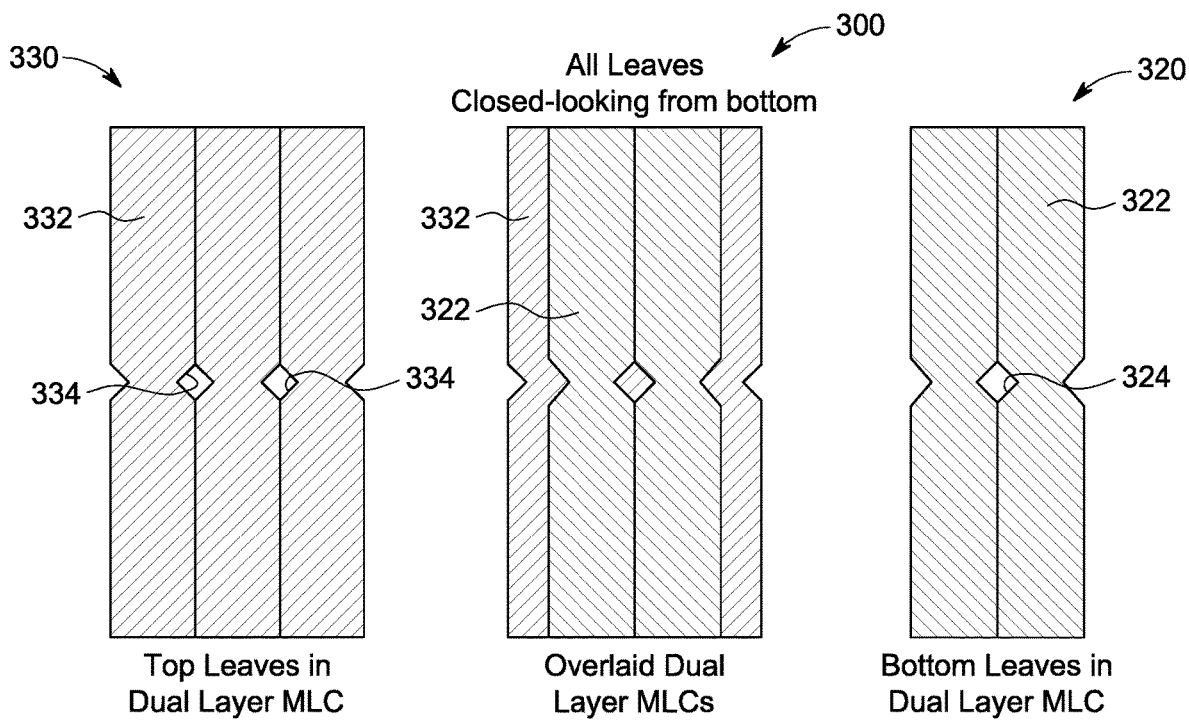
Top Leaves in Dual Layer MLC
FIG. 4A
Overlaid Dual Layer MLCs
FIG. 4B
Bottom Leaves in Dual Layer MLC
FIG. 4C
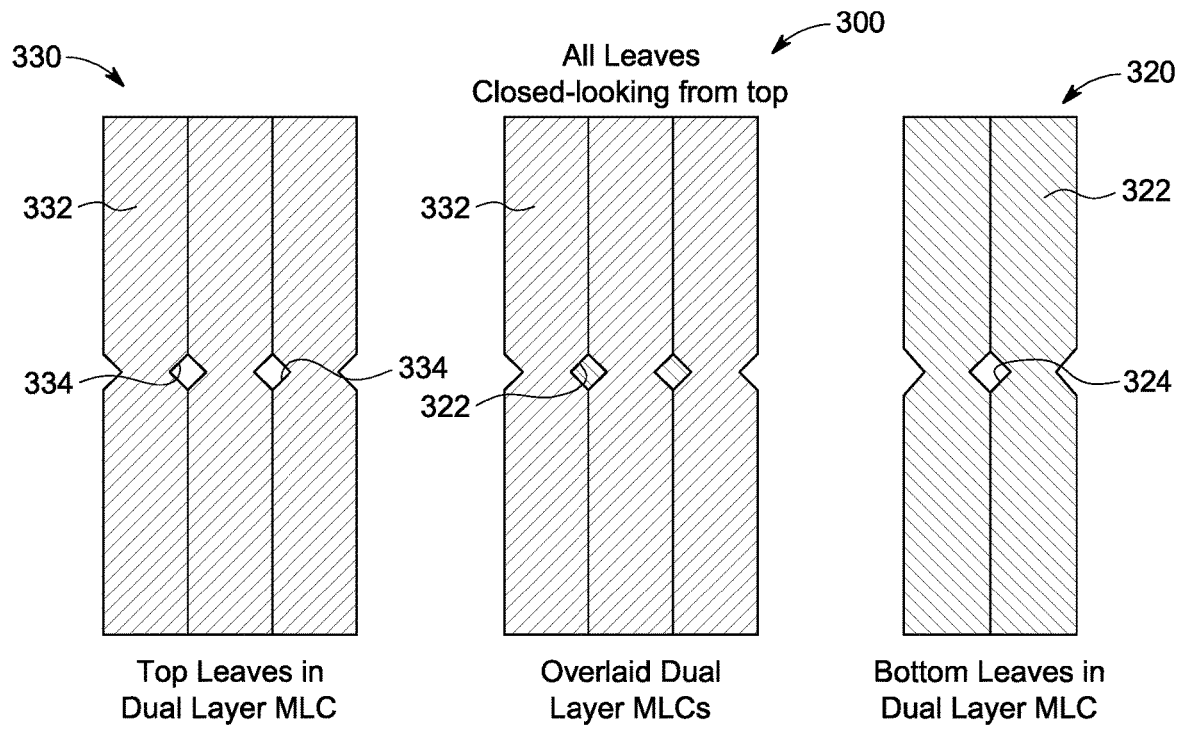
Top Leaves in Dual Layer MLC
FIG. 5A
Overlaid Dual Layer MLCs
FIG. 5B
Bottom Leaves in Dual Layer MLC
FIG. 5C Top Leaves in
Dual Layer MLC Overlaid Dual
Layer MLCs Bottom Leaves in
Dual Layer MLC Top Leaves in
Dual Layer MLC Overlaid Dual
Layer MLCs Bottom Leaves in
Dual Layer MLC

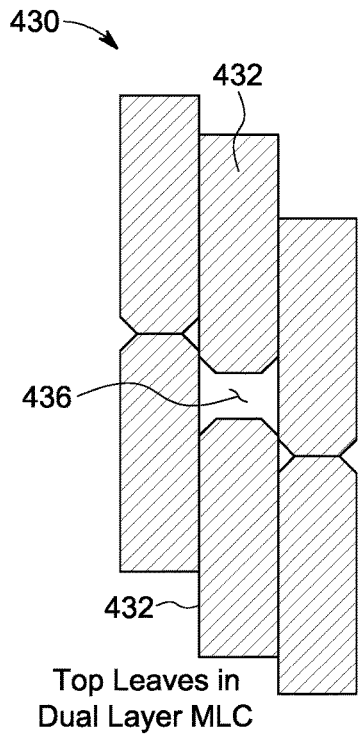
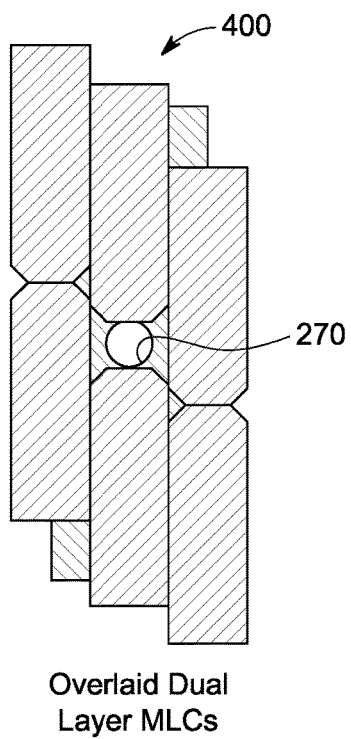
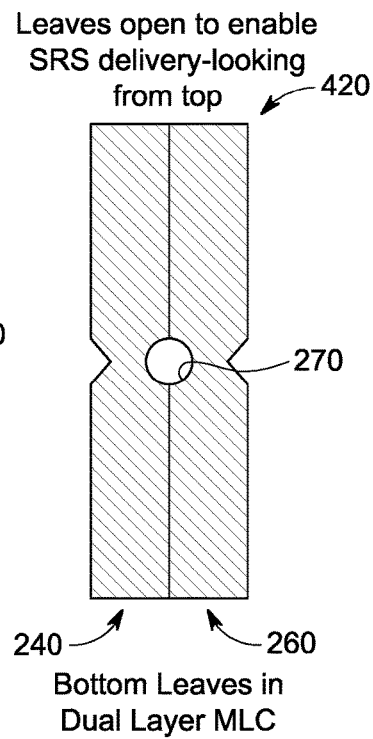
Top Leaves in Dual Layer MLC
FIG. 9A
Overlaid Dual Layer MLCs
FIG. 9B
Bottom Leaves in Dual Layer MLC
FIG. 9C
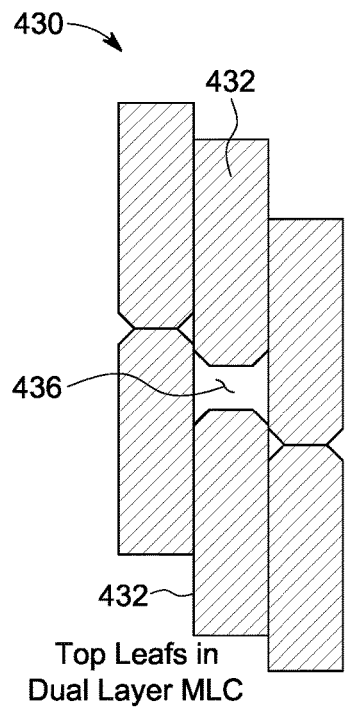
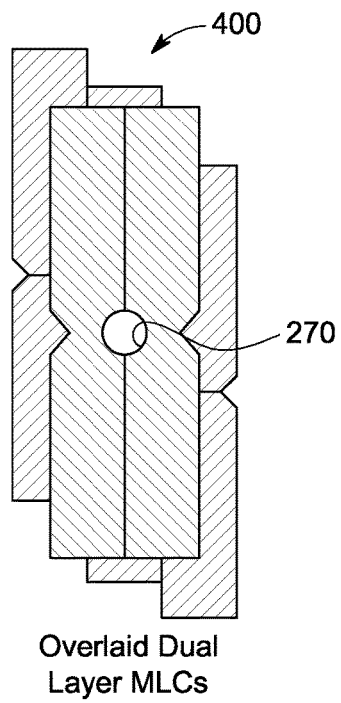
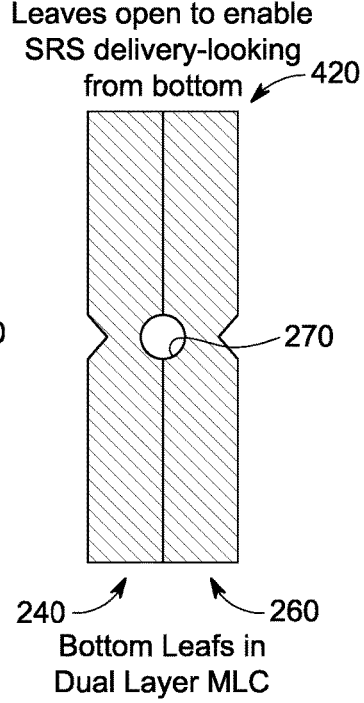
Top Leafs in Dual Layer MLC
FIG. 10A
Overlaid Dual Layer MLCs
FIG. 10B
Bottom Leafs in Dual Layer MLC
FIG. 10C

MULTILEAF COLLIMATOR CONE ENABLING STEREOTACTIC RADIOSURGERY

CROSS REFERENCE TO RELATED APPLICATIONS

This application is a continuation of U.S. application Ser. No. 17/153,161 filed Jan. 20, 2021 entitled "Multileaf Collimator Cone Enabling Stereotactic Radiosurgery," which is a division of U.S. application Ser. No. 16/399,828 filed Apr. 30, 2019 entitled "Ser. No. 16/399,828," the disclosures of all of which are hereby incorporated by reference in their entirety.

TECHNICAL FIELD

This disclosure relates generally to radiation apparatuses and methods. In particular, various embodiments of multileaf collimators (MLCs) enabling and enhancing radiosurgery and stereotactic radiosurgery are described.

BACKGROUND

Radiosurgery is a highly precise, intensified form of radiation therapy. Stereotactic radiosurgery (SRS) is generally known as application of high doses of radiation in a single fraction based on specially defined treatment coordinates. Stereotactic radiotherapy is similar to SRS but with the exception that typically two or more fractions are used for patient treatments. It is worth noting that the term stereotactic may imply use of a stereotactic coordinate system for patient localization for treatment. Over time, image guided procedures and other forms of patient and tumor localization which do not rely on stereotactic coordinates have fallen in the category of stereotactic procedures even though by classical definitions the stereotactic localization method is not employed.

Conventionally, SRS cones are used to help achieve precise delivery of high dose of radiation. SRS cones are typically made from tungsten and have a conical hole through which radiation can pass providing a focused treatment beam. SRS cones can be mounted externally to an interface mount on a linear accelerator or internally on a positioning device in the treatment head. Inclusion of SRS cones in a treatment head requires more space for installation and complex motion axes. If mounted externally, SRS cones may present potential collision hazard with treatment couch or patient and generally involve compromises in efficiency of treatment delivery.

U.S. Patent Application Publication No. 2017-0197094 discloses a "virtual cone" approach using a multileaf collimator (MLC). According to the "virtual cone" approach, an MLC is used to form an actual elongated aperture through which radiation is delivered to a target volume at a first orientation of the MLC. Then, the MLC is rotated to a second orientation and radiation is delivered to the target volume through the actual elongated aperture. A relatively large cumulative dose of radiation can be thus delivered to the target volume through a "virtual cone" created by an area of overlap between the actual elongated apertures at the first and second MLC orientations. The "virtual cone" approach requires double passes of an MLC per couch angle and the general MLC leaf shape designed for other purposes may result in compromises in the shape of delivered radiation and may cause concerns of users that it may not produce robust implementation of radiation delivery.

SUMMARY

A multileaf collimator is provided comprising a plurality of beam-blocking leaves arranged side by side in a first bank and a plurality of beam-blocking leaves arranged side by side in a second bank opposite to the first bank. At least one of the beam-blocking leaves in the first bank is provided with a first through-hole configured to allow a radiation beam to pass through for radiosurgery. The first through-hole may have a generally truncated cone shape or cylindrical shape. As used herein, a truncated cone refers to a result of cutting a cone by a plane parallel to the base and removing the part containing the apex.

An apparatus is provided comprising a first multileaf collimator including a plurality of pairs of beam-blocking leaves each comprising an end portion. The end portions of beam-blocking leaves of two adjacent pairs are configured to collectively form an aperture when the two adjacent pairs of beam-blocking leaves are closed. The aperture may have a generally circular shape in a beam's eye view.

A radiosurgery method using a multi-level multileaf collimator (MLC) is provided. The multi-level MLC comprises a first MLC having a plurality of pairs of beam-blocking leaves in a first level and a second MLC having a plurality of pairs of beam-blocking leaves in a second level. At least two adjacent pairs of beam-blocking leaves in the first MLC have end portions configured to collectively form a first aperture when the two adjacent pairs of beam-blocking leaves are closed. The method comprises opening a pair of beam-blocking leaves in the second MLC overlaying the at least two adjacent pairs of beam-blocking leaves of the first MLC to form a second aperture in the second MLC, where the second aperture in the second MLC has a size greater than the size of the first aperture in the first MLC; closing the plurality of pairs of beam-blocking leaves of the first MLC, whereby the beam-blocking leaves of the two adjacent pairs of the first MLC partially block the second aperture in the second MLC, allowing the first aperture in the first MLC to control the size and/or shape of a radiation beam passing through the multi-level MLC; and delivering the radiation beam to a target volume through the multi-level MLC, whereby the radiation beam delivered to the target volume is sized and shaped by the first aperture in the first MLC.

This Summary is provided to introduce selected aspects and embodiments of this disclosure in a simplified form and is not intended to identify key features or essential characteristics of the claimed subject matter, nor is it intended to be used as an aid in determining the scope of the claimed subject matter. The selected aspects and embodiments are presented merely to provide the reader with a brief summary of certain forms the invention might take and are not intended to limit the scope of the invention. Other aspects and embodiments of the disclosure are described in the section of Detailed Description.

BRIEF DESCRIPTION OF THE DRAWINGS

These and various other features and advantages will become better understood upon reading of the following detailed description in conjunction with the accompanying drawings provided below, where:

FIGS. 4A-4C are bottom views of a multi-level MLC including beam-blocking leaves shown in FIGS. 3A-3B where all of the leaves are closed. FIG. 4A is a bottom view of the top MLC. FIG. 4C is a bottom view of the bottom MLC. FIG. 4B is a bottom view of the overlaid top and bottom MLCs.

FIGS. 5A-5C are top views of a multi-level MLC including beam-blocking leaves shown in FIGS. 3A-3B where all of the beam-blocking leaves are closed. FIG. 5A is a top view of the top MLC. FIG. 5C is a top view of the bottom MLC. FIG. 5B is a top view of the overlaid top and bottom MLCs.

FIG. 6A is a bottom view of the top MLC showing that a pair of beam-blocking leaves are opened. FIG. 6C is a bottom view of the bottom MLC showing that the beam-blocking leaves are closed. FIG. 6B is a bottom view of the overlaid top and bottom MLCs showing an aperture formed therein enabling SRS delivery.

FIG. 7A is a top view of the top MLC showing that a pair of beam-blocking leaves are opened. FIG. 7C is a top view of the bottom MLC showing that the beam-blocking leaves are closed. FIG. 7B is a top view of the overlaid top and bottom MLCs showing an aperture formed therein enabling SRS delivery.

FIGS. 9A-9C illustrate a method of providing stereotactic radiotherapy using a multi-level MLC including beam-blocking leaves shown in FIGS. 8A-8B. FIG. 9A is a top view of the top MLC showing that a pair of beam-blocking leaves are opened. FIG. 9C is a top view of the bottom MLC showing that the beam-blocking leaves are closed. FIG. 9B is a top view of the overlaid top and bottom MLCs showing an aperture formed therein enabling SRS delivery.

FIGS. 10A-10C illustrate a method of providing stereotactic radiotherapy using a multi-level MLC including beam-blocking leaves shown in FIGS. 8A-8B. FIG. 10A is a bottom view of the top MLC showing that a pair of beam-blocking leaves are opened. FIG. 10C is a bottom view of the bottom MLC showing that the beam-blocking leaves are closed. FIG. 10B is a bottom view of the overlaid top and bottom MLCs showing an aperture formed therein enabling SRS delivery.

DETAILED DESCRIPTION OF EMBODIMENTS

Embodiments of this disclosure provide solutions for radiosurgery and stereotactic radiosurgery using specially designed multileaf collimators (MLCs). One exemplary approach is to configure or modify the MLC leaf tips so that they form a small cone when the MLC leaves are closed and/or are more conducive to cone-like profiles than are conventional MLCs with "virtual cone." Another exemplary approach is to provide one or more through-holes in one or more MLC leaves. The solutions provided by this disclosure enable delivery of small SRS cone-like beam profiles directly from an MLC while fully preserving the general purpose or functionality of the MLC.

Referring to FIGS. 1-14, various embodiments of multi-leaf collimators (MLCs) that enable and enhance radiosurgery and stereotactic radiosurgery (SRS) will now be described.

Figure 1:
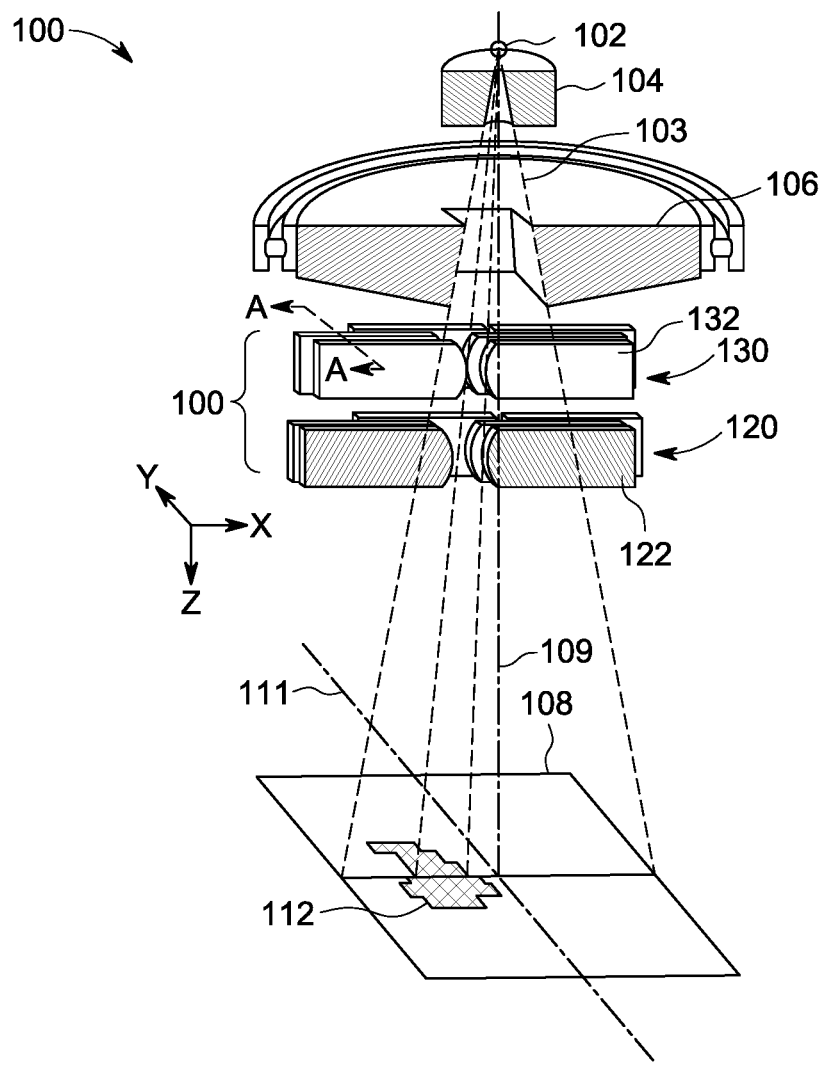
FIG. 1 is a simplified illustration of a radiation system including a multileaf collimator (MLC) in accordance with embodiments of this disclosure.

FIG. 1 is a simplified illustration of a radiation system including an MLC according to embodiments of the disclosure. As shown, the radiation system 100 may include a radiation source 102 configured to produce a beam 103 of radiation such as photons, electrons, protons, or other types of radiation. For example, the radiation source 102 may include a metallic target configured to produce a beam of x-rays upon impingement of electrons. The radiation system 100 may include various beam shaping components such as a primary collimator 104 and optionally a secondary collimator 106 to generally limit the extent of the beam 103 as it travels away from the source 102 toward an isocenter plane 108. An MLC 110 such as a multi-level MLC is disposed between the source 102 and the isocenter plane 108 to further shape the beam, as indicated by the shaped field 112 in the isocenter plane 108, according to a general use embodiment of the MLC. The MLC 110 may rotate about the beamline or axis 109 passing through the source 102, placing the MLC in various orientations. The source 102, primary collimator 104, secondary collimator 106, and the MLC 110 may be enclosed in a treatment head (not shown), which can be rotated by a gantry (not shown) about an axis such as a horizontal axis 111. Thus, the radiation system 100 can deliver treatment beams to a target in the isocenter plane 108 from various angles. The shape, size, and/or intensity of the beam 103 can be adjusted or dynamically adjusted by the MLC 110 as the beam angle is stepped or swept around the target.

The MLC 110 may be a single level MLC or a multi-level MLC as shown. By way of example, the MLC 110 may include a first MLC 120 in a first level distal to the source 102 and a second MLC 130 in a second level proximal to the source 102. As used herein, the term "multileaf collimator" or "MLC" refers to a collection of a plurality of beam-blocking leaves each of which can be longitudinally moved in and out of a beam to modify one or more parameters of the beam such as the beam shape, size, energy, or intensity etc. Each beam-blocking leaf may be driven by a motor with a lead screw or other suitable means. The beam-blocking leaves may be arranged in pairs. The beam-blocking leaves of each pair may be brought in contact or retracted from each other to close or open a path for a radiation beam to pass through the MLC. The beam-blocking leaves may be arranged in opposing banks and supported by a frame, box, carriage or other support structure, which has features allowing the individual beam-blocking leaves to extend into and retract from the beam. The frame, box, carriage or other support structure can be further moved or translated in addition to the individual leaf travel.

As shown in FIG. 1, the first and second MLCs 120, 130 may be arranged such that the moving direction of individual beam-blocking leaves of the first and second MLCs 120, 130 are generally in parallel. For example, as shown in FIG. 1 the beam-blocking leaves 122 of the first MLC 120 in the first level are longitudinally movable in the x-direction, and the beam-blocking leaves 132 of the second MLC 130 in the second level are also longitudinally movable in the x-direction. Alternatively, the first and second MLCs may be arranged such that the moving direction of the beam-blocking leaves of the first MLC is non-parallel e.g. perpendicular to the moving direction of the beam-blocking leaves of the second MLC.

Figure 2:
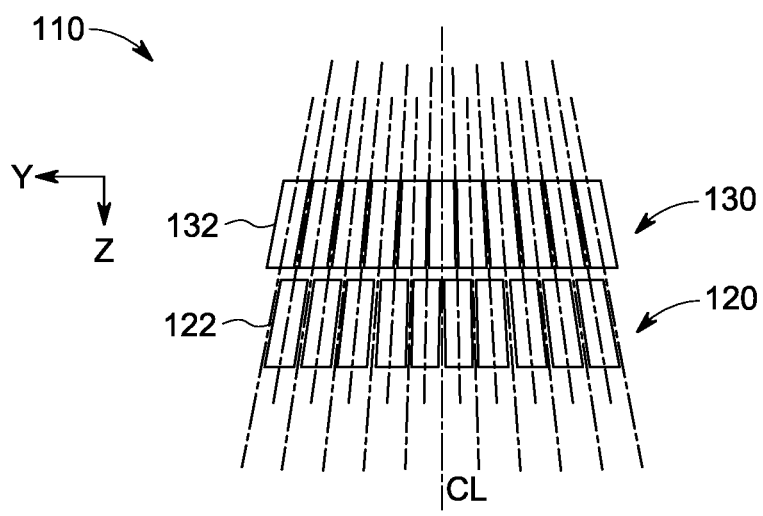
FIG. 2 is a cross-sectional view of the exemplary MLC shown in FIG. 1, taken along line A-A.

The first and second MLCs 120, 130 may be arranged such that the leaves 132 of the second MLC 130 may laterally offset the leaves 122 of the first MLC 120 in a beam's eye view, or as viewed in a direction from the source 102. FIG. 2 is a cross-sectional view of a portion of the multi-level MLC 110 of FIG. 1 taken along line A-A, showing the lateral offset arrangement of the leaves of the multi-level MLC 110. As shown, a leaf 132 of the second MLC 130 in the second level offsets a leaf 122 of the first MLC 120 in the first level as viewed from the source 102. By way of example, a leaf 132 of the second MLC 130 may offset a leaf 122 of the first MLC 120 by substantially half a leaf. Alternatively, a gap between two adjacent leaves 132 of the second MLC 130 in the second level may be positioned substantially at the middle of a leaf 122 of the first MLC 120. The lateral offset arrangement of leaves in different levels provides for leaf projections that are also offset at the isocenter plane. Therefore, the lateral offset arrangement of leaves may provide for substantially an equivalent of doubling MLC definition, or improving the resolution to half as compared to the definition of a single level MLC with leaves of the same physical width. In some embodiments, three or more MLCs may be arranged in three or more levels such that each leaf at a level may offset e.g. by ⅓ or 1/n of a leaf width as projected at the isocenter plane where n is the number of the MLCs. U.S. Pat. No. 8,637,841 issued on Jan. 28, 2014 to the common assignee entitled "Multi Level Multileaf Collimators" describes various embodiments of multi-level MLCs, the disclosure of which is incorporated herein by reference in its entirety.

The beam-blocking leaves 122, 132 of the first and second MLCs 120, 130 may have various leaf tip profiles or end portion configurations. For ease of description of the leaf tip profiles and the MLC in general, in the Detailed Description and appended Claims, the term "top view" may be used interchangeably with the term "beam's eye view" to refer to a view observed from the source or in a direction parallel to the beamline. The term "bottom view" may be used to refer to a view opposite to the top view of the leaf tip profile. The term "side view" may be used to describe a view observed from a side surface of the leaf tip profile.

In some embodiments, the beam-blocking leaves of the MLC 110 may have a flat front-end surface. In both a side view and a beam's eye view, a leaf tip with a flat front-end surface may be shown to have a straight line orthogonal to the leaf longitudinal moving direction and two right angles at each side of the straight line. In some embodiments, the beam-blocking leaves of the MLC 110 may have a curved front-end surface. In a side view, a leaf with a curved front-end surface may be shown to have a curved line with a radius and two parallel lines at either side of the curved line. In a top view, a leaf with a curved front-end surface may be shown to have a straight line orthogonal to the leaf longitudinal moving direction and two right angles on each side of the straight line. In the Detail Description and appended Claims, the term "square shape" may be used to describe a leaf tip profile which, in a top view, has a straight line orthogonal to the leaf longitudinal moving direction and two right angles at each side of the straight line. The term "non-square shape" may be used to describe any leaf tip profile which, in a top view, does not have a square shape. The non-square shape in a top view may include a curved or elliptic shape or a shape of a chamfer leaf which may include a combination of a straight portion and a beveled portion at each side of the straight portion as will be described in greater detail below.

In some embodiments of this disclosure, the beam-blocking leaves of the MLC 110 may have a tip profile that includes a combination of a curved surface portion and a beveled or flat surface portion at each side of the curved surface portion. The term "chamfer leaf" may be used herein to refer to a leaf which includes a combination of a curved end surface portion and beveled or flat end surface portions at either side of the curved end surface portion.

Figure 3A:
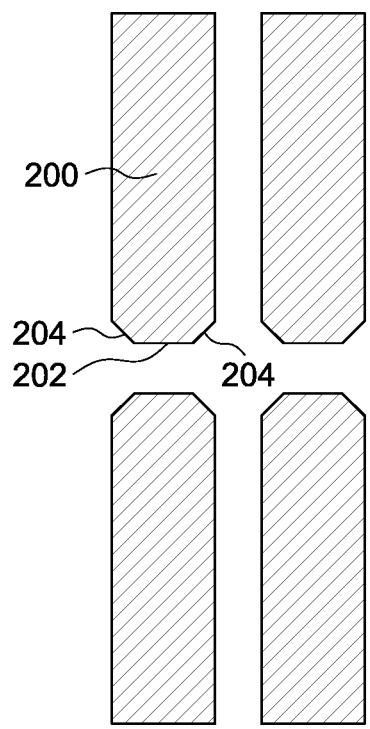
FIG. 3A depicts exemplary beam-blocking leaves of two adjacent pairs where the leaves of each pair are opened or retracted showing the leaf tip profiles.
Figure 3B:
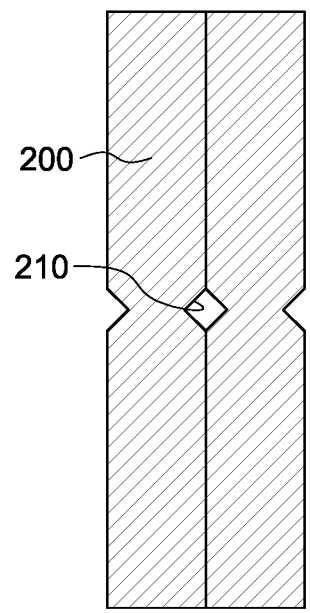
FIG. 3B depicts exemplary beam-blocking leaves of two adjacent pairs where the leaves of each pair are closed forming an aperture.

FIGS. 3A-3B are top views of exemplary beam-blocking leaves 200 according to embodiments of this disclosure. FIG. 3A shows two adjacent pairs of beam-blocking leaves 200 when the leaves of each pair are retracted or opened. It should be noted that in FIG. 3A, the gap between the sides of the adjacent pairs of the leaves is exaggerated for purpose of illustrating the leaf tip profiles with greater clarity. FIG. 3B shows two adjacent pairs of beam-blocking leaves 200 when the leaves of each pair are brought into contact or closed forming an aperture 210.

As shown in FIG. 3A, in a top view or beam's eye view, the end portion or tip of a beam-blocking leaf 200 may be shown to have a straight middle line section 202 orthogonal to the leaf longitudinal moving direction and beveled or angled lines sections 204 at each side of the straight middle line section 202. The term "chamfer angle" may be used herein to refer to the angle between the beveled line 204 and the straight line 202. For example, the straight middle line section 202 of a leaf in a beam's eye view may be approximately 50% of the leaf width, and the remaining 25% at each side of the middle section can be shaped in any different chamfer angles optimized for various different field slopes. The chamfer angles may range from 5-95 degrees, or from 10-90 degrees, or from 20-80 degrees, or from 40-60 degrees. In one example, the chamfer angle may be about 45 degrees. In another example, the chamfer angle may be about 60 degrees. In a specific embodiment, a beam-blocking leaf may have a straight middle line section about 50% of the leaf width, with the remaining 25% at each side being beveled with a chamfer angle of about 45 or 60 degrees.

As shown in FIG. 3B, when two adjacent pairs of beam-blocking leaves 200 are brought in contact or closed, an aperture 210 is formed collectively by the end portions of four adjacent beam-blocking leaves 200. The aperture 210 may extend from the top of the leaves to the bottom of the leaves or the height of the leaves forming a path for a radiation beam. The size and/or shape of the aperture 210 may be defined by the tip profile of the beam-blocking leaves 200. For example, the chamfer angle, the leaf thickness, the leaf thickness, and the ratio of the beveled section to the middle section etc. may be selected so that the aperture 210 formed may have a size and shape suitable for SRS delivery. By way of example, the aperture 210 formed by the beam-blocking leaves 200 when closed may have a rectangular or square shape in a top view as shown in FIG. 3B or an effective rectangular prism shape extending from the top to the bottom of the leaves. The side of the square of the aperture 210 is therefore smaller than the thickness of the individual beam-blocking leaves 200. By way of example, the aperture 210 may have a square shape in a top view having a side dimension ranging from 2 to 10 millimeter.

FIGS. 4A-4C, 5A-5C, 6A-6C, and 7A-7C illustrate an embodiment of a method of providing stereotactic radiosurgery (SRS) using a multi-level MLC 300 according to the disclosure. The multi-level MLC 300 may include a first or bottom MLC 320 and a second or top MLC 330 comprising beam-blocking leaves shown in FIGS. 3A-3B. The bottom and top MLCs 320, 330 can be arranged such that the longitudinal moving direction of the beam-blocking leaves 322 of the bottom MLC 320 is generally parallel with the longitudinal moving direction of the beam-blocking leaves 332 of the top MLC 330. The first and second MLCs 320, 330 can be arranged such that the beam-blocking leaves 332 of the top MLC 330 laterally offset the beam-blocking leaves 322 of the bottom MLC 320 e.g. by about half or a third of a leaf width. For clarity, only three pairs of beam-blocking leaves 332 in the top MLC 330 and only two pairs of beam-blocking leaves 322 in the bottom MLC 320 are shown. It should be noted that the bottom and top MLC 320, 330 may include more than two or three pairs of beam-blocking leaves.

FIGS. 4A-4C are bottom views of the MLCs 300. FIG. 4A is a bottom view of the top MLC 330, FIG. 4C a bottom view of the bottom MLC 320, and FIG. 4B a bottom view of the overlaid top and bottom MLCs 300. As shown in FIG. 4A, the use of beam-blocking leaves 332 in the top MLC 330 results in apertures 334 when all the leaves 332 are closed. Similarly, as shown in FIG. 4C, the use of beam-blocking leaves 322 in the bottom MLC 320 results in aperture 324 when all the leaves are closed. Nevertheless, because of the lateral-offset arrangement of the top and bottom MLCs 330, 320, the apertures 334 in the top MLC 330 are blocked by the beam-blocking leaves 322 of the bottom MLC 320, and the aperture 324 in the bottom MLC 320 is blocked by the beam-blocking leaves 332 of the top MLC 330, as shown in FIG. 4B. Therefore, when all beam-blocking leaves 332 of the top MLC 330 and all beam-blocking leaves 322 of the bottom MLC 320 are closed, no beam path is formed in the multi-level MLC 300 as shown in FIG. 4B, accomplishing a general functionality of the MLC.

FIGS. 5A-5C are top views of the MLCs 300. FIG. 5A is a top view of the top MLC 330, FIG. 5C a top view of the bottom MLC 320, and FIG. 5B a top view of the overlaid top and bottom MLCs 300. As shown in FIG. 5A, the use of beam-blocking leaves 332 in the top MLC 330 result in apertures 334 when all the beam-blocking leaves 332 are closed. Similarly, as shown in FIG. 5C, the use of beam-blocking leaves 322 in the bottom MLC 320 result in aperture 324 when all the beam-blocking leaves 322 are closed. Nevertheless, because of the lateral-offset arrangement of the top and bottom MLCs 330, 320, the apertures 334 in the top MLC 320 are blocked by the beam-blocking leaves 322 of the bottom MLC 320, and the aperture 324 in the bottom MLC 320 is blocked by the beam-blocking leaves 332 of the top MLC 300, as shown in FIG. 5B. Therefore, when all beam-blocking leaves 332 of the top MLC 330 and all beam-blocking leaves 322 of the bottom MLC 320 are closed, no beam path is formed in the multi-level MLC 300 as shown in FIG. 4B, accomplishing a general functionality of the MLC.

Figure 6A:
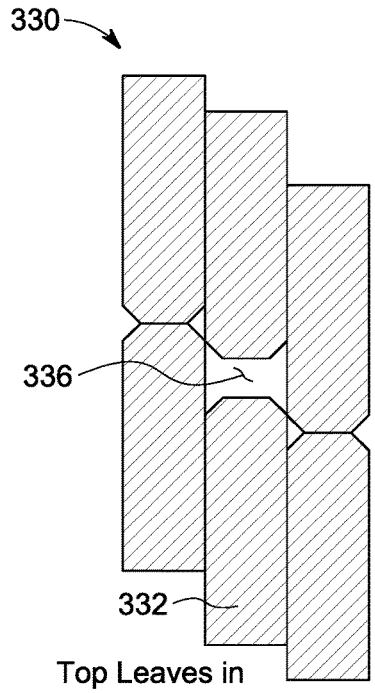
FIGS. 6A-6C illustrate a method of providing stereotactic radiosurgery (SRS) using a multi-level MLC including beam-blocking leaves shown in FIGS. 3A-3B.
Figure 6B:
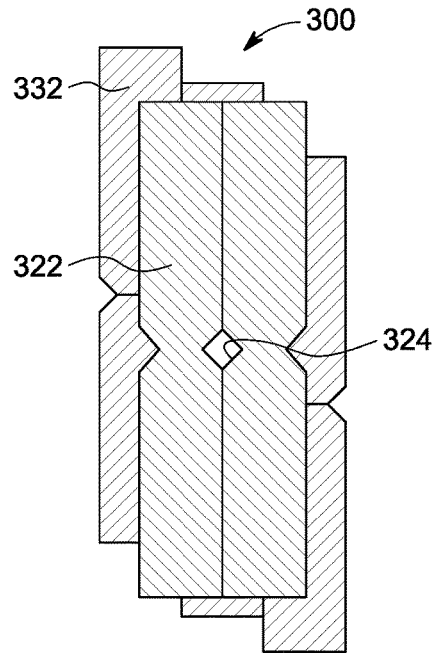
Figure 6C:
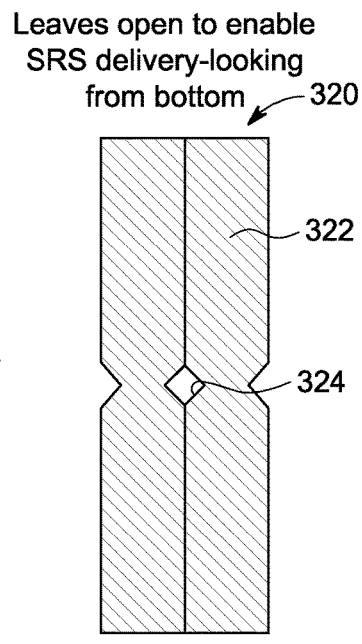

FIGS. 6A-6C are bottom views of the top MLC 330 (FIG. 6A), bottom MLC 320 (FIG. 6C), and overlaid top and bottom MLCs 300 (FIG. 6B) illustrating a method of providing radiosurgery according to an embodiment of the disclosure. MLCs 330 and 320 may include beam-blocking leaves shown in FIGS. 3A-3B. According to the embodiment of the method, a pair of beam-blocking leaves 332 in the top MLC 330 can be retracted or opened, forming an aperture 336 of a greater size in the top MLC 330, as shown in FIG. 6A. The beam-blocking leaves 322 in the bottom MLC 320 can be closed, resulting in an aperture 324 due to the use of beam-blocking leaves shown in FIGS. 3A-3B. FIG. 6B shows that the aperture 324 in the bottom MLC 320 is exposed to the aperture 336 of greater size 336 in the top MLC 330. The lateral-offset arrangement of the top and bottom MLCs 330, 320 allows the beam-blocking leaves 322 of the bottom MLC 320 to partially block the aperture 336 in the top MLC 330. Therefore, when a pair of beam-blocking leaves 332 in the top MLC 330 is opened and all the other leaves in the top and bottom MLCs 330, 320 are closed, the aperture 324 in the bottom MLC 320 is exposed, forming a path to allow a radiation beam passing through the multi-level MLC 300. The size and shape of the aperture 324 control the size and shape of the radiation beam, enabling SRS delivery.

Figure 7A:
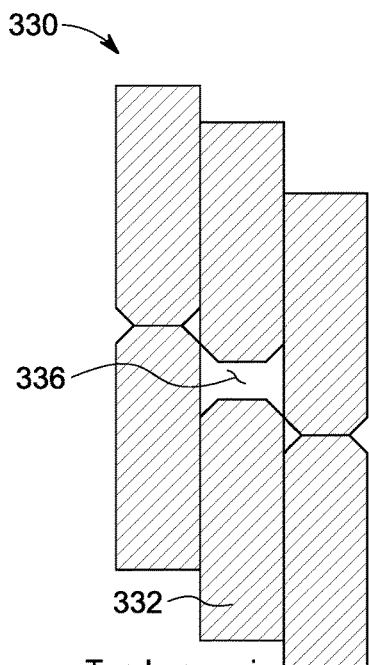
FIGS. 7A-7C illustrate a method of providing stereotactic radiotherapy (SRS) using a multi-level MLC including beam-blocking leaves shown in FIGS. 3A-3B.
Figure 7B:
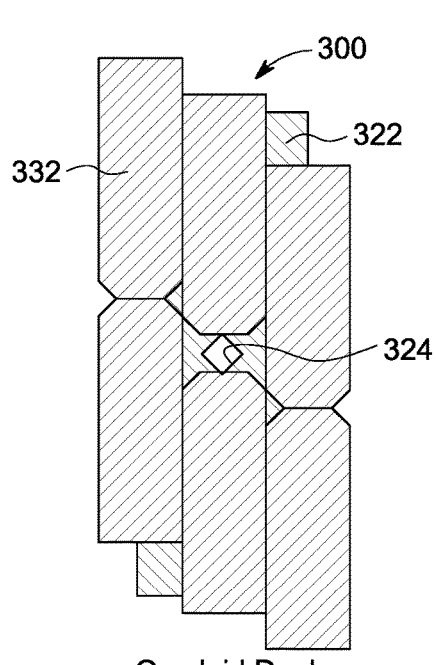
Figure 7C:
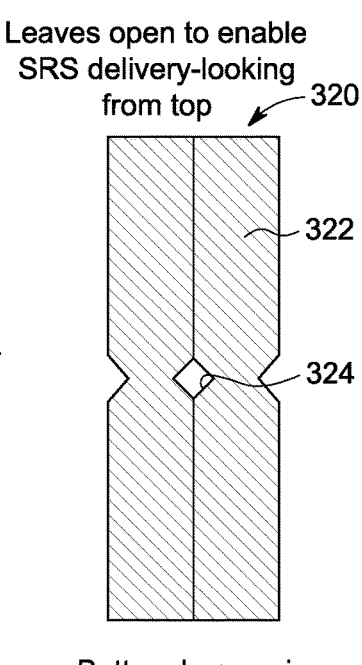

FIGS. 7A-7C are top views of the top MLC 330 (FIG. 7A), bottom MLC 320 (FIG. 7C), and overlaid top and bottom MLCs 300 (FIG. 7B) illustrating the method of providing radiosurgery which has been described above in conjunction with the bottom views of FIGS. 6A-6C. For completeness, a pair of beam-blocking leaves 332 in the top MLC 330 can be retracted or opened, forming an aperture 336 of a greater size in the top MLC 330, as shown in FIG. 7A. The beam-blocking leaves 322 in the bottom MLC 320 can be closed, resulting in an aperture 324 due to the use of beam-blocking leaves shown in FIGS. 3A-3B. FIG. 7B shows that the aperture 324 in the bottom MLC 320 is exposed to the aperture 336 of greater size 336 in the top MLC 330. The lateral-offset arrangement of the top and bottom MLCs 330, 320 allows the beam-blocking leaves 322 of the bottom MLC 320 to partially block the aperture 336 in the top MLC 330. Therefore, when a pair of beam-blocking leaves 332 in the top MLC 330 is opened and all the other leaves in the top and bottom MLCs 330, 320 are closed, the aperture 324 in the bottom MLC 320 is exposed, forming a path to allow a radiation beam passing through the multi-level MLC 300. The size and shape of the aperture 324 control the size and shape of the radiation beam, enabling SRS delivery.

In the method illustrated in FIGS. 6A-6C and 7A-7C, the aperture 324 formed in the multilevel MLC 300 can be aligned with the beam's central axis. By way of example, when in use, a pair of beam-blocking leaves in the middle or proximate to the middle of the top MLC 330 can be retracted as shown in FIGS. 6A and 7A, allowing the aperture 324 in the bottom MLC 320 to be aligned with the beam's central axis. The support structure of the MLC may also be moved relative to the source in aligning the aperture with the beam's central axis. It should be noted that the capability of aligning the aperture 324 with the beam's central axis, while preferred, is not required. The aperture 324 can be placed off the beam's central axis as long as it is within the beam divergence. A patient support or couch can be moved to align the target in the patient to be treated with the focused radiation beam passing through the aperture.

Figure 8A:
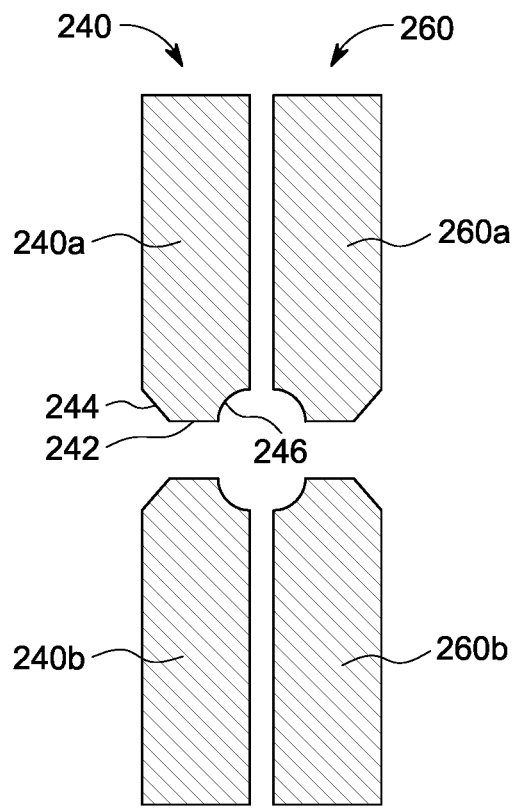
FIG. 8A depicts exemplary beam-blocking leaves of two adjacent pairs where the leaves of each pair are opened or retracted showing the leaf tip profiles according to embodiments of the disclosure.
Figure 8B:
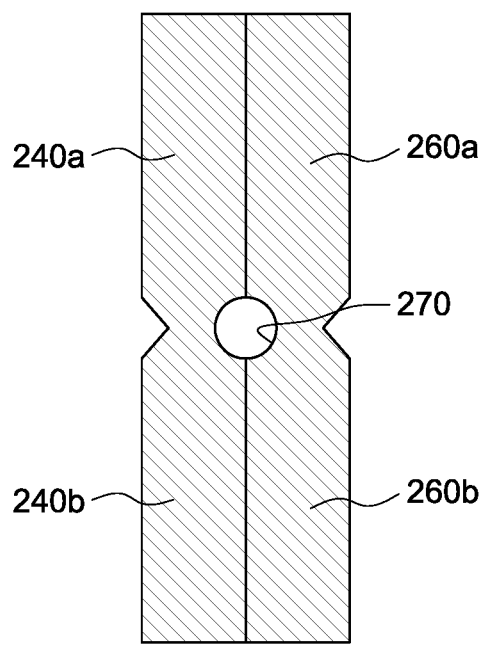
FIG. 8B illustrates the beam-blocking leaves of the two adjacent pairs where the leaves of each pair are closed forming an aperture.

In some embodiments of the disclosure, an MLC may comprise two adjacent pairs of beam-blocking leaves having leaf tip profiles shown in FIGS. 8A-8B. The leaf tips or end portions of the beam-blocking leaves can be configured such that an aperture having a generally truncated cone shape or cylindrical shape or an equivalent of truncated cone or cylindrical shape is formed when the beam-blocking leaves are closed. In a top view or beam's eye view, the aperture formed may have a circular shape.

Referring to FIGS. 8A-8B, for example, leaf 240*a* of pair 240 may have a leaf tip profile including a concave surface portion extending from the top to the bottom of the leaf or the height of the leaf. In a beam's eye view, the concave surface portion will be shown to have a curved line section 246, as shown in FIG. 8A. Therefore, the end portion of leaf 240*a* may be configured so that in a beam's eye view, the tip of leaf 240*a* may be shown to have a straight middle line section 242 perpendicular to the leaf longitudinal moving direction, a beveled line section 244 at one side of the middle line section, and a curved line section 246 at another side of the middle line section. In a specific embodiment, the curved line section 246 may constitute a quarter-circle line.

Leaf 240*b* of pair 240 may have a leaf tip profile that is a mirror image of the leaf tip profile of the opposing leaf 240*a*. Therefore, when the leaves 240*a*, 240*b* of pair 240 are closed, a semi-circle line can be formed by the quarter-circle lines of leaves 240*a* and 240*b* in a beam's eye view, as illustrated in FIG. 8B. Likewise, leaf 260*b* of the adjacent pair 260 may have a leaf tip profile that is a mirror image of the leaf tip profile of opposing leaf 260*a* so that when the leaves 260*a*, 260*b* of the adjacent pair 260 are closed, a semi-circle line is formed by the quarter-circle lines of leaves 260*a* and 260*b*. When the two adjacent pairs of four beam-blocking leaves 240*a*, 240*b* and 260*a*, 260*b* are closed, a circle is formed by the quarter-circle lines of leaves 240*a*, 240*b* and 260*a*, 260*b* in the beam's eye view.

In some embodiments, the concave surface portions of the beam-blocking leaves 240*a*, 240*b* and 260*a*, 260*b* of the two adjacent pairs can be configured so that the aperture 270 formed when the beam-blocking leaves are closed has a generally cylindrical shape. In some embodiments, the concave surface portions of the beam-blocking leaves 240*a*, 240*b* and 260*a*, 260*b* of the two adjacent pairs can be configured so that the aperture 270 formed when the beam-blocking leaves are closed has a generally truncated cone shape. In some embodiments, the front-end portions of the beam-blocking leaves 240*a*, 240*b* and 260*a*, 260*b* of the two adjacent pairs can be configured so that the aperture 270 formed when the beam-blocking leaves are closed projects a circular shape on the isocenter plane, providing an equivalent of a truncated cone or cylindrical hole.

The pairs of beam-blocking leaves 240*a-b*, 260*a-b* shown in FIGS. 8A-8B may be disposed in the middle or proximate to the middle of the plurality of beam-blocking leaves of the MLC. Such arrangement may facilitate alignment of the aperture 270 with the beam's central axis when in use. Alternatively, the pairs of beam-blocking leaves 240*a-b*, 260*a-b* shown in FIGS. 8A-8B may not be disposed at the middle of the MLC leaves. The alignment with the aperture 270 can be achieved by moving the support structure of the MLC or moving the patient support or couch.

FIGS. 9A-9C and 10A-10C illustrate an embodiment of a method of providing stereotactic radiotherapy using a multi-level MLC 400 according to the disclosure. The multi-level MLC 400 comprises a first or bottom MLC 420 and a second or top MLC 430. The bottom MLC 420 may comprise two adjacent pairs of the beam-blocking leaves having leaf tip profiles as shown in FIGS. 8A-8B. The remaining pairs of the beam-blocking leaves of the bottom and top MLCs may have leaf tip profiles as shown in FIGS. 3A-3B. The bottom MLC 420 and top MLC 430 may be arranged such that the longitudinal moving direction of the beam-blocking leaves of the bottom MLC 420 is generally parallel with the longitudinal moving direction of the beam-blocking leaves of the top MLC 430. The bottom and top MLCs 420, 430 can be arranged such that the beam-blocking leaves of the top MLC 430 laterally offset the beam-blocking leaves of the bottom MLC 420 e.g. by about half or a third of a leaf width. For clarity, only three pairs of beam-blocking leaves in the top MLC 430 and only two pairs of beam-blocking leaves in the bottom MLC 420 are shown. It should be noted that the bottom and top MLC 420, 430 may include more than two or three pairs of beam-blocking leaves.

FIGS. 9A-9C are top views of the top MLC 430 (FIG. 9A), bottom MLC 420 (FIG. 9C), and overlaid top and bottom MLCs 400 (FIG. 9B). FIGS. 10A-10C are bottom views of the top MLC 430 (FIG. 10A), bottom MLC 420 (FIG. 10C), and overlaid top and bottom MLCs 400 (FIG. 10B). According to an embodiment of the method, a pair of beam-blocking leaves 432 in the top MLC 430 can be retracted or opened, forming an aperture 436 of a greater size in the top MLC 430, as shown in FIGS. 9A and 10A. The beam-blocking leaves 240, 260 in the bottom MLC 420 can be closed, resulting in an aperture 270 due to the use of the beam-blocking leaves 240*a*, 240*b*, 260*a*, and 260*b* as shown in FIGS. 8A-8B. The aperture 270 may have a shape of a circle in a top or bottom view as shown in FIGS. 9C and 10C. FIGS. 9B and 10B show that the aperture 270 in the bottom MLC 420 is exposed to the aperture 436 of greater size in the top MLC 430. The lateral-offset arrangement of the top and bottom MLCs 430, 420 allows the beam-blocking leaves 240, 260 of the bottom MLC 420 to partially block the aperture 436 in the top MLC 430. Therefore, when a pair of beam-blocking leaves 432 in the top MLC 430 is opened and all the other leaves in the top and bottom MLCs 430, 420 are closed, the aperture 270 in the bottom MLC 420 is exposed, forming a path to allow a radiation beam passing through the multi-level MLC 400. The aperture 270 controls the size and shape of the radiation beam, enabling SRS delivery.

Figure 11:
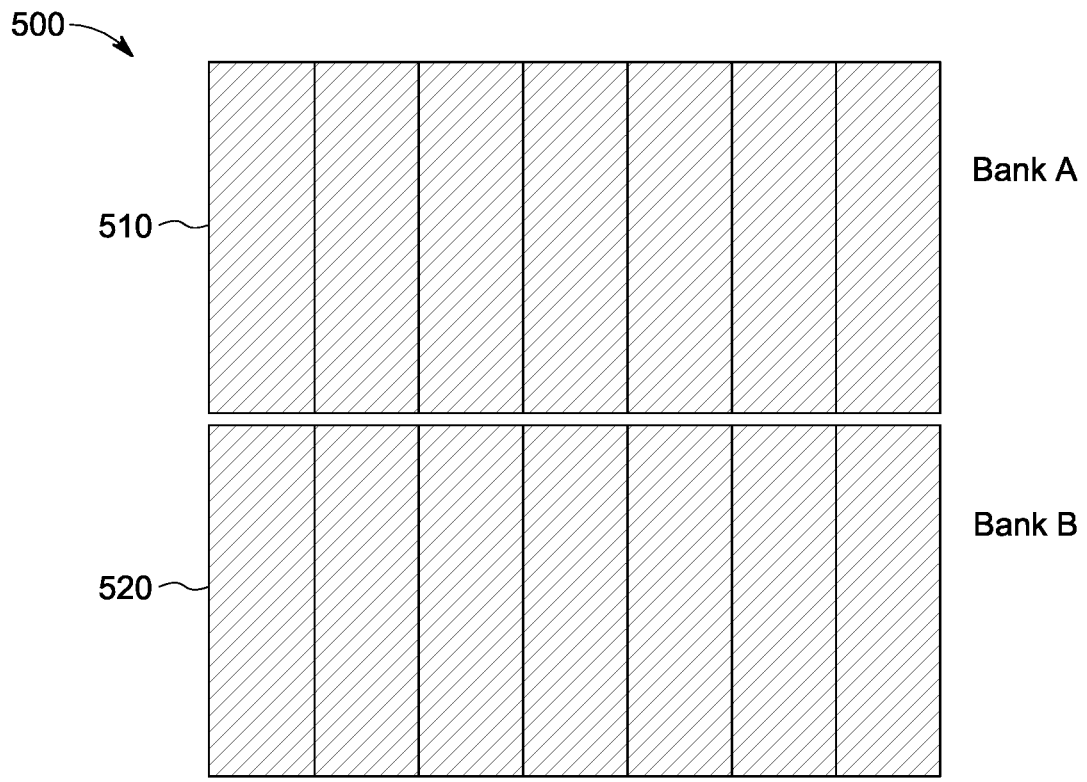
FIG. 11 depicts an exemplary MLC comprising beam-blocking leaves arranged in two opposing banks.

Referring now to FIGS. 11-14, alternative embodiments of multileaf collimators of the disclosures are now described. FIG. 11 depicts a multileaf collimator 500 comprising a plurality of beam-blocking leaves 510 arranged side by side in a first bank (Bank A) and a plurality of beam-blocking leaves 520 arranged side by side in a second bank (Bank B) opposite to the first bank (Bank A). Each of the plurality of beam-blocking leaves 510, 520 in the first and second banks is longitudinally movable.

Figure 12:
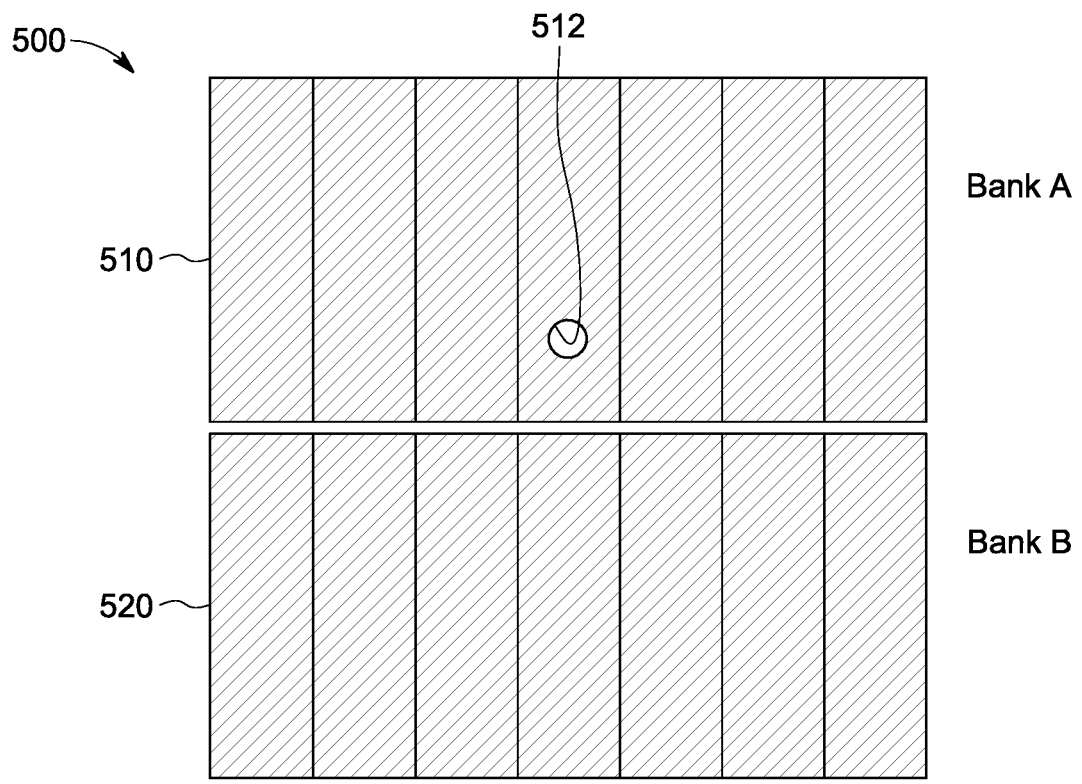
FIG. 12 depicts an exemplary MLC according to embodiments of the disclosure where a through-hole is provided in a beam-blocking leaf in a bank.

According to embodiments of the disclosure, a beam-blocking leaf in the first bank may be provided with a first through-hole 512 as shown in FIG. 12. The first through-hole 512 may be sized and shaped, or configured, to allow a radiation beam to pass through the MLC 500 when in use for stereotactic radiosurgery. By way of example, the first through-hole 512 may have a generally truncated cone shape, a generally cylindrical shape, or any other regular or irregular shapes. The size of the first through-hole in a cross-section may range from 2 to 10 millimeters, 4 to 8 millimeters, or any other dimensions generally suitable for stereotactic radiosurgery. In a specific embodiment, the first through-hole may be sized so that a circle with a diameter of about 4 or 5 millimeters may be projected on the isocenter plane. As used herein, the term "about" includes variances within 1 millimeter of the size referred to. The beam-blocking leaf provided with the first through-hole 512 may be disposed in the middle or proximate to the middle of the plurality of beam-blocking leaves in the first bank (Bank A), as shown in FIG. 12. Such arrangement can facilitate alignment of the first through-hole with the beam's central axis when in use. For example, when in use the beam-blocking leaf provided with the first through-hole 512 may be longitudinally moved or extended to align the center of the through-hole with the beam's central axis. The support structure of the MLC may also be moved relative to the source in aligning the through-hole with the beam's central axis. It should be noted that the capability of aligning the through-hole with the beam's central axis, while preferred, is not required. In some embodiments, the beam-blocking leaf provided with a through-hole may not be disposed at the middle of the beam-blocking leaves of the MLC. Further, the through-hole can be placed off the beam's central axis as long as it is within the beam divergence when in use. A patient support or couch can be moved to align the target in the patient to be treated with the focused radiation beam passing through the through-hole.

Figure 13:
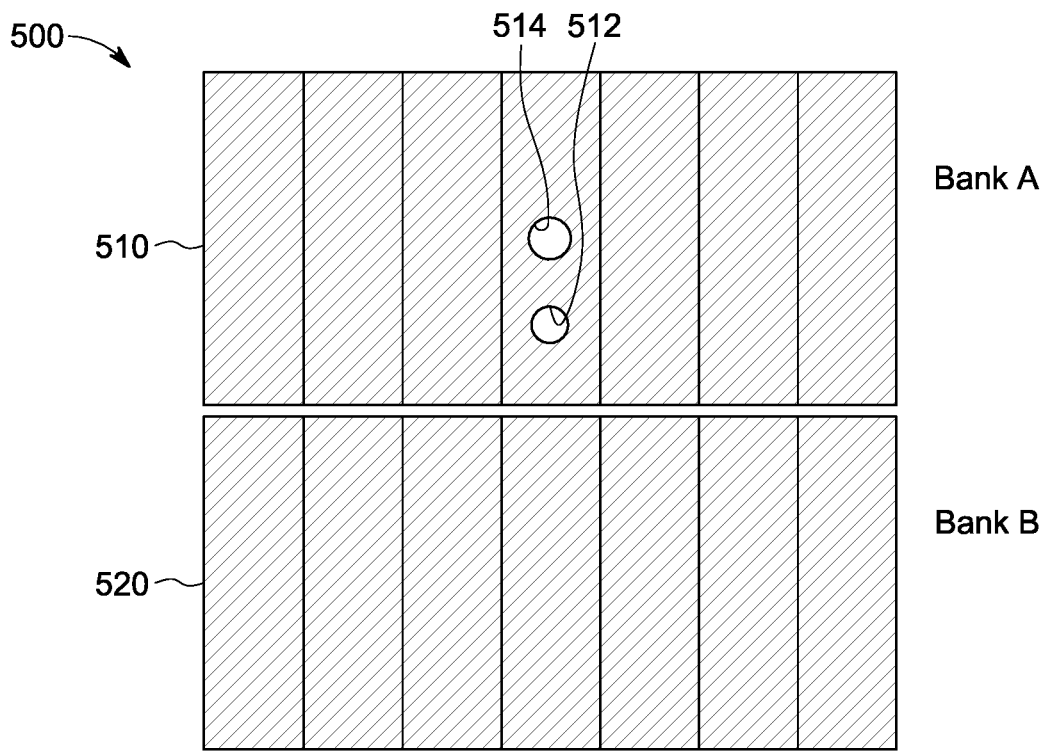
FIG. 13 depicts an exemplary MLC according to embodiments of the disclosure where two through-holes of different sizes are provided in a beam-blocking leaf in a bank.

In some embodiments, the beam-blocking leaf provided with the first through-hole 512 may be further provided with a second through-hole 514 as shown in FIG. 13. The second through-hole 514 may be configured to allow a radiation beam to pass through the MLC 500 when in use for stereotactic radiosurgery. The size of the second through-hole 514 may be different from or same as the size of the first through-hole 512. The shape of the second through-hole 514 may be the same or different from the shape of the first through-hole 512. FIG. 13 shows an embodiment where the first and the second through-holes 512, 514 are provided in a same beam-blocking leaf in a bank. Alternatively, the first and second through-holes may be provided in different beam-blocking leaves in a same bank.

Figure 14:
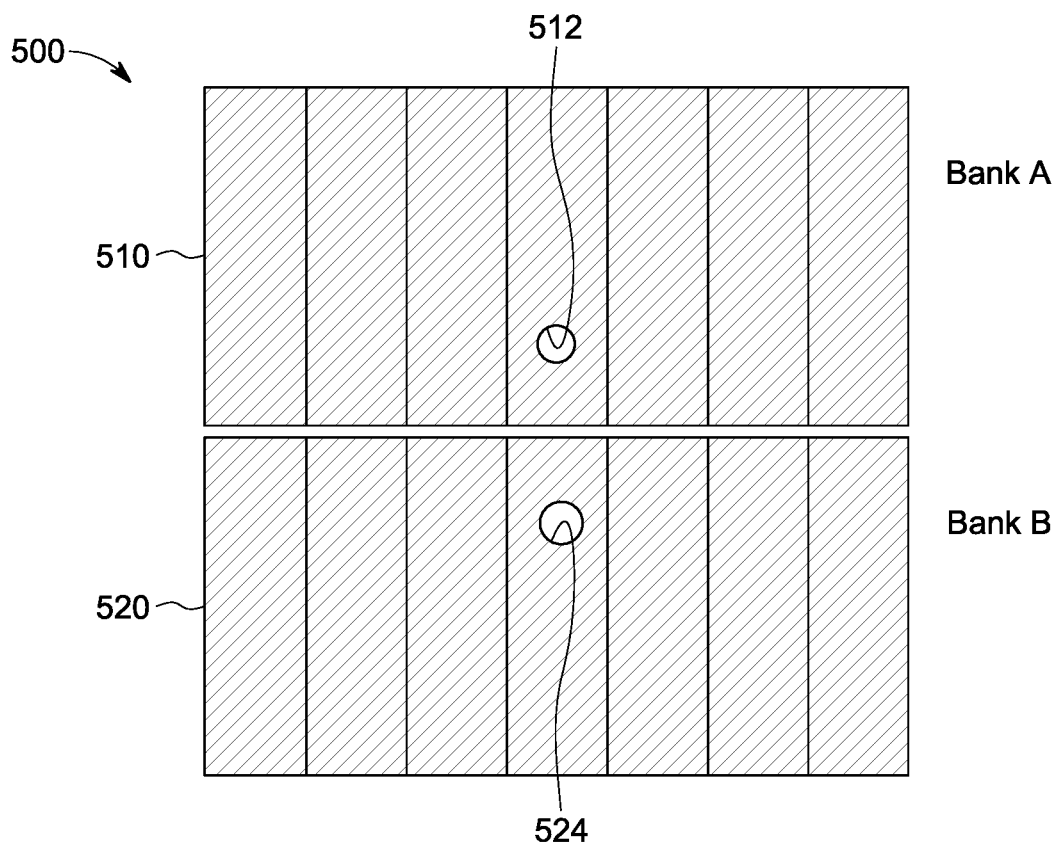
FIG. 14 depicts an exemplary MLC according to embodiments of the disclosure where a first through-hole is provided in a beam-blocking leaf in a bank and a second through-hole of a different size is provided in a beam-blocking leaf in the opposing bank.

According to alternative embodiments of the disclosure, a beam-blocking leaf in the first bank (Bank A) is provided with a first through-hole 512 and a beam-blocking leaf in the second bank (Bank B) is provided with a second through-hole 524, as shown in FIG. 14. The beam-blocking leaves provided with the first and second through-holes 512, 524 may be paired and longitudinally movable relative to each other. Alternatively, the beam-blocking leaves provided with the first and second through-holes are not paired. The first and second through-holes 512, 524 may be each configured to allow a radiation beam to pass through the MLC 500 when in use for stereotactic radiosurgery. The size of the second through-hole 524 may be different from or same as the size of the first through-hole 512 in the opposing beam-blocking leaf. The shape of the second and first through-holes 512, 524 in the opposing beam-blocking leaves may be same or different. By way of example, the second and first through-holes may have a generally truncated cone shape, a generally cylindrical shape, or any other regular or irregular shapes respectively. The size of the second and first through-holes in a cross-section may range from 2 to 10 millimeters, 4 to 8 millimeters, or any other suitable dimensions respectively.

Various embodiments of MLCs enabling and enhancing radiosurgery or stereotactic radiosurgery are described. Advantageously, the "MLC cone" solution provided by this disclosure enables delivery of radiosurgery or stereotactic radiosurgery while preserving the broad scope or general functionality of the MLCs in shaping radiation beams for other applications by using measures such as additional blocking or treatment planning system. The "MLC cone" solution can deliver beam profiles generally comparable to those provided by conventional SRS cones. The efficiency of delivery is better than conventional "virtual cone" solution because double pass per couch angle would not be needed. The through-hole(s) in an MLC provided by this disclosure ensures consistent accuracy in delivery as compared to the conventional "virtual cone" approach which suffers from inaccurate delivery arising from the inconsistency in MLC positioning. The "MLC cone" solution provided by this disclosure can also appease the users who do not believe in the conventional "virtual cone" approach. The "MLC cone" solution is much more equivalent to SRS cone beam profiles and can produce more robust implementation requiring less quality assurance (QA).

Accordingly, a multileaf collimator is provided comprising a plurality of beam-blocking leaves arranged side by side in a first bank and a plurality of beam-blocking leaves arranged side by side in a second bank opposite to the first bank. At least one of the beam-blocking leaves in the first bank is provided with a first through-hole configured to allow a radiation beam to pass through for radiosurgery. The first through-hole may have a generally truncated cone shape or cylindrical shape. As used herein, a truncated cone refers to a result of cutting a cone by a plane parallel to the base and removing the part containing the apex.

In some embodiments, at least one of the beam-blocking leaves in the second bank is provided with a second through-hole configured to allow a radiation beam to pass through for radiosurgery. The second through-hole may have a size different from the size of the first through-hole. The second through-holes may have a generally truncated cone shape or cylindrical shape.

In some embodiments, the beam-blocking leaf provided with the first through-hole in the first bank may be further provided with a second through-hole configured to allow a radiation beam to pass through for radiosurgery. The second through-hole may have a size different from the size of the first through-hole.

An apparatus is provided comprising a first multileaf collimator including a plurality of pairs of beam-blocking leaves each comprising an end portion. The end portions of beam-blocking leaves of two adjacent pairs are configured to collectively form an aperture when the two adjacent pairs of beam-blocking leaves are closed. The aperture may have a generally circular shape in a beam's eye view.

In some embodiments, the end portions of the beam-blocking leaves of the two adjacent pairs may be configured to form the aperture having a generally truncated cone shape or cylindrical shape.

In some embodiments, the apparatus may further comprise a second multileaf collimator including a plurality of pairs of beam-blocking leaves. The first multileaf collimator may be arranged in a first level and the second multileaf collimator may be arranged in a second level. The beam-blocking leaves of the first multileaf collimator are longitudinal movable in a first direction and the beam-blocking leaves of the second multileaf collimator are longitudinal movable in a second direction generally parallel with the first direction. Each of the beam-blocking leaves of the second multileaf collimator laterally offsets a beam-blocking leaf of the first multileaf collimator in a beam's eye view.

In some embodiments, the beam-blocking leaves of the second multileaf collimator have a tip profile in the beam's eye view comprising a middle line section orthogonal to the second direction and a beveled line section at each side of the middle line section. The beam-blocking leaves may have a chamfer angle formed between the beveled line and the middle line ranging from 20-80 degrees.

In some embodiments, the first multileaf collimator includes, in addition to the beam-blocking leaves of the two adjacent pairs, beam-blocking leaves having a tip profile in the beam's eye view comprising a middle line section orthogonal to the first direction and a beveled line section at each side of the middle line section. The end portions of the beam-blocking leaves of the two adjacent pairs may have a tip profile in the beam's eye view comprising a middle line section orthogonal to the first direction, a beveled line section at a side of the middle line section, and a quarter-circular line section at another side of the middle line section.

A radiosurgery method using a multi-level multileaf collimator (MLC) is provided. The multi-level MLC comprises a first MLC having a plurality of pairs of beam-blocking leaves in a first level and a second MLC having a plurality of pairs of beam-blocking leaves in a second level. At least two adjacent pairs of beam-blocking leaves in the first MLC have end portions configured to collectively form a first aperture when the two adjacent pairs of beam-blocking leaves are closed. The method comprises opening a pair of beam-blocking leaves in the second MLC overlaying the at least two adjacent pairs of beam-blocking leaves of the first MLC to form a second aperture in the second MLC, where the second aperture in the second MLC has a size greater than the size of the first aperture in the first MLC; closing the plurality of pairs of beam-blocking leaves of the first MLC, whereby the beam-blocking leaves of the two adjacent pairs of the first MLC partially block the second aperture in the second MLC, allowing the first aperture in the first MLC to control the size and/or shape of a radiation beam passing through the multi-level MLC; and delivering the radiation beam to a target volume through the multi-level MLC, whereby the radiation beam delivered to the target volume is sized and shaped by the first aperture in the first MLC.

In some embodiments, the end portions of the beam-blocking leaves of the two adjacent pairs of the first MLC may be configured so that the first aperture formed has a generally rectangular shape in a beam's eye view. In some embodiments, the end portions of the beam-blocking leaves of the two adjacent pairs of the first MLC may be configured so that the first aperture formed may have a generally circular shape in a beam's eye view.

Various embodiments have been described with reference to the figures. It should be noted that some figures are not necessarily drawn to scale. The figures are only intended to facilitate the description of specific embodiments, and are not intended as an exhaustive description or as a limitation on the scope of the disclosure. Further, in the figures and description, specific details may be set forth in order to provide a thorough understanding of the disclosure. It will be apparent to one of ordinary skill in the art that some of these specific details may not be employed to practice embodiments of the disclosure. In other instances, well known components or process steps may not be shown or described in detail in order to avoid unnecessarily obscuring embodiments of the disclosure.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise. Further, the term "first" or "second" etc. may be used to distinguish one element from another in describing various similar elements. It should be noted the terms "first" and "second" as used herein include references to two or more than two. Further, the use of the term "first" or "second" should not be construed as in any particular order unless the context clearly dictates otherwise.

Various relative terms such as "upper," "above," "top," "over," "on," "below," "under," "bottom," "higher," "lower" or similar terms may be used herein for convenience in describing relative positions, directions, or spatial relationships in conjunction with the drawings. The use of the relative terms should not be construed as to imply a necessary positioning, orientation, or direction of the structures or portions thereof in manufacturing or use, and to limit the scope of the invention.

Various embodiments of radiosurgery methods are described in connection with the drawings. It will be appreciated that more or fewer steps, actions, or processes may be incorporated into the methods without departing from the scope of the disclosure. No particular order is implied by the steps described herein. It further be appreciated that the methods described in conjunction with drawings may be embodied in machine-executable instructions (e.g. software). The instructions can be used to cause a general-purpose or special-purpose processor that is programmed with the instructions to perform the operations described. Alternatively, the operations might be performed by specific hardware components that contain hardwired logic for performing the operations, or by any combination of programmed computer components and custom hardware components. The methods may be provided as a computer program product that may include a machine-readable medium having stored thereon instructions that may be used to program a computer (or other electronic devices) to perform the methods. For the purposes of this specification, the term "machine-readable medium" shall be taken to include any medium that is capable of storing or encoding a sequence of instructions for execution by the machine and that causes the machine to perform any one of the methodologies of the present invention. The term "machine-readable medium" shall accordingly be taken to include, but not be limited to, solid-state memories, optical and magnetic disks. Furthermore, it is common in the art to speak of software, in one form or another (e.g., program, procedure, process, application, module, logic, etc.), as taking an action or causing a result. Such expressions are merely a shorthand way of saying that execution of the software by a computer causes the processor of the computer to perform an action or produce a result.

Various embodiments of radiosurgery methods and apparatuses have been described. Those skilled in the art will appreciate that various other modifications may be made. For example, in a multilevel MLC, an SRS aperture may be formed in the bottom MLC as described above in connection with FIGS. 4A-10C. Alternatively, or additionally, an SRS aperture may be formed in the top MLC. All these or other variations and modifications are contemplated by the inventors and within the scope of the invention.

What is claimed is:

1. An apparatus, comprising:
a first multileaf collimator including a first plurality of pairs of first beam-blocking leaves each including an end surface, wherein the end surfaces of first beam-blocking leaves of two adjacent pairs have a first concave surface portion configured to collectively form an aperture when the two adjacent pairs of beam-blocking leaves are closed, and the end surfaces of first beam-blocking leaves other than the two adjacent pairs are chamfer leaves have a combination of a first convex surface portion and a first beveled flat surface portion at either side of the first convex surface portion; and a second multileaf collimator including a second plurality of pairs of second beam-blocking leaves, the second beam-blocking leaves of the second multileaf collimator including chamfer leaves having a combination of a second convex surface portion and a second beveled flat surface portion at either side of the second convex surface portion.

2. The apparatus of claim 1, wherein the aperture formed has a size allowing a beam of radiation passing therethrough for stereotactic radiosurgery (SRS).

3. The apparatus of claim 1, wherein the aperture formed has a shape allowing a beam of radiation passing therethrough to project a field of a generally circular shape on a plane.

4. The apparatus of claim 1, wherein the first concave surface portion of each of the first beam-blocking leaves of the two adjacent pairs are configured to collectively form the aperture in a generally truncated cone or cylindrical shape.

5. The apparatus of claim 1, wherein the first concave surface portion of the first beam-blocking leaves of one of the two adjacent pairs are mirror images of the first concave surface portion of the other one of the two adjacent pairs.

6. The apparatus of claim 1, wherein the end surface of each of the first beam-blocking leaves of the two adjacent pairs further include a flat surface portion.

7. The apparatus of claim 6, wherein the end surfaces of the first beam-blocking leaves of the two adjacent pairs further include a convex surface portion.

8. The apparatus of claim 1, wherein the end surface of each of the first beam-blocking leaves of the two adjacent pairs further include a convex surface portion.

9. The apparatus of claim 1, wherein the two adjacent pairs are disposed in or proximate to a middle of the first plurality of pairs of the first multileaf collimator.

10. The apparatus of claim 1, wherein the first multileaf collimator is arranged in a first level and the second multileaf collimator is arranged in a second level;

the first beam-blocking leaves of the first multileaf collimator are longitudinally movable in a first direction, the second beam-blocking leaves of the second multileaf collimator are longitudinally movable in a second direction generally parallel with the first direction; and each of the second beam-blocking leaves of the second multileaf collimator laterally offsets a first beam-blocking leaf of the first multileaf collimator.

11. The apparatus of claim 10, wherein the first concave surface portion of the first beam-blocking leaves of one of the two adjacent pairs of the first multileaf collimator are mirror images of the first concave surface portion of the other one of the two adjacent pairs of the first multileaf collimator.

12. The apparatus of claim 1, wherein the chamfer leaves of the second multileaf collimator have a chamfer angle ranging from 20-80 degrees.

13. The apparatus of claim 1, wherein the chamfer leaves of the first multileaf collimator have a chamfer angle substantially same as the chamfer angle of the chamfer leaves of the second multileaf collimator.

14. The apparatus of claim 1, wherein the end surface of each of the first beam-blocking leaves of the two adjacent pairs of the first multileaf collimator further include a convex surface portion and a beveled flat surface portion at a side of the convex surface portion.

15. The apparatus of claim 14, wherein the first concave surface portion of each of the first beam-blocking leaves of the two adjacent pairs of the first multileaf collimator are configured to collectively form the aperture in a generally truncated cone or cylindrical shape.

16. The apparatus of claim 1, wherein the first multileaf collimator is arranged in a first level and the second multileaf collimator is arranged in a second level; and the first beam-blocking leaves of the first multileaf collimator are longitudinally movable in a first direction, the second beam-blocking leaves of the second multileaf collimator are longitudinally movable in a second direction generally non-parallel with the first direction.

17. The apparatus of claim 16, wherein the aperture formed has a size allowing a beam of radiation passing therethrough for stereotactic radiosurgery (SRS).

18. The apparatus of claim 17, wherein the aperture formed has a configuration allowing the beam of radiation passing therethrough to project a field of a generally circular shape on a plane.

* * * * *